US008742137B2

(12) United States Patent
Mecfel-Marczewski et al.

(10) Patent No.: US 8,742,137 B2
(45) Date of Patent: Jun. 3, 2014

(54) 2-OXO-1, 3-DIOXOLANE-4-CARBOXYLIC ACID AND DERIVATIVES THEREOF, THEIR PREPARATION AND USE

(75) Inventors: Joanna Mecfel-Marczewski, Altenmarkt an der Alz (DE); Burkhard Walther, Garching (DE); Jochen Mezger, Garching an der Alz (DE); Radoslaw Kierat, Altenmarkt (DE); Rosita Staudhamer, Babensham (DE)

(73) Assignee: Construction Research & Technology GmbH, Trostberg (DE)

( * ) Notice: Subject to any disclaimer, the term of this patent is extended or adjusted under 35 U.S.C. 154(b) by 87 days.

(21) Appl. No.: 13/162,967

(22) Filed: Jun. 17, 2011

(65) Prior Publication Data

US 2011/0313177 A1   Dec. 22, 2011

Related U.S. Application Data

(60) Provisional application No. 61/355,566, filed on Jun. 17, 2010.

(51) Int. Cl.
*C07D 317/26* (2006.01)
*C07D 317/36* (2006.01)
*C07D 317/38* (2006.01)

(52) U.S. Cl.
CPC ............ *C07D 317/36* (2013.01); *C07D 317/38* (2013.01)
USPC ....................................................... 549/229

(58) Field of Classification Search
CPC ............................ C07D 317/36; C07D 317/38
USPC ....................................................... 549/229
See application file for complete search history.

(56) References Cited

U.S. PATENT DOCUMENTS 7,968,572 B2 * 6/2011 Nakai et al. ................... 514/340

FOREIGN PATENT DOCUMENTS

| EP | 0 001 088 A1 | 3/1979 |
| EP | 1 941 946 A1 | 7/2008 |
| JP | 7-285960 A | 10/1995 |
| JP | 2006/003433 A | 1/2006 |
| WO | WO 2004/003001 A1 | 1/2004 |
| WO | WO2007/040208 * | 4/2007 |

OTHER PUBLICATIONS

Watanabe, STN record of JP 2006-003433, published 2006.*
Diakoumakos, Constantino, et al., "Non-Isocyanate-Based Polyurethanes Derived upon the Reaction of Amines with Cyclocarbonate Resins", Macromol. Symp., 2004, vol. 216, pp. 37-46.
Petit, Y., et al., "Ethyl Glycidate From (S)-Serine: Ethyl (R)-(+)-2,3-Epoxypropanoate", Organic Synthesis Collection, 2004, vol. 10, p. 401; Organic Syntheses, 1998, vol. 75, p. 37.
Stevenson, Christian P., et al., "Preparation of (S)-Methyl Glycidate VIA Hydrolytic Kinetic Resolution", Organic Syntheses, 2006, vol. 83, pp. 162-169; Organic Syntheses Collection, 2009, vol. 11, pp. 157-163.
Tomita, Hidetoshi, et al, "Model Reaction for the Syntheis of Polyhydroxyurethanes from Cyclic Carbonates with Amines: Substituent Effect on the Reactivity and Selectivity of Ring-Opening Direction in the Reaction of Five-Membered Cyclic Carbonates with Amine", Journal of Polymer Science: Part A: Polymer Chemistry, 2001, vol. 39, pp. 3678-3685.
PCT/EP2011/058945—International Search Report, Nov. 15, 2011.
PCT/EP2011/058945—International Written Opinion, Jul. 6, 2011.
PCT/EP2011/058945—International Preliminary Report on Patentability, Jul. 27, 2012.

* cited by examiner

*Primary Examiner* — Rebecca Anderson
*Assistant Examiner* — Karen Cheng
(74) *Attorney, Agent, or Firm* — Curatolo Sidoti Co., LPA; Joseph G. Curatolo; Salvatore A. Sidoti

(57) ABSTRACT

Proposed are 2-oxo-1,3-dioxolane-4-carboxylic acid and derivatives thereof, according to the following formula,

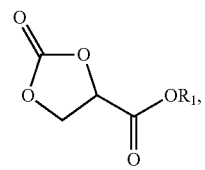

in which $R_1$ represents a negative charge, hydrogen or can be preferably Me or Et or a radical having a valency of 2 to 5, which is substituted with an amount of further 2-oxo-1,3-dioxolane-4-carboxyl groups equal to the radical valency minus 1, as well as a process for their preparation by means of carboxylation of the corresponding epoxides, a process for their transesterification and their use for the preparation of hydroxyurethanes and as end groups for the blocking of amines.

13 Claims, 3 Drawing Sheets

Figure 1:
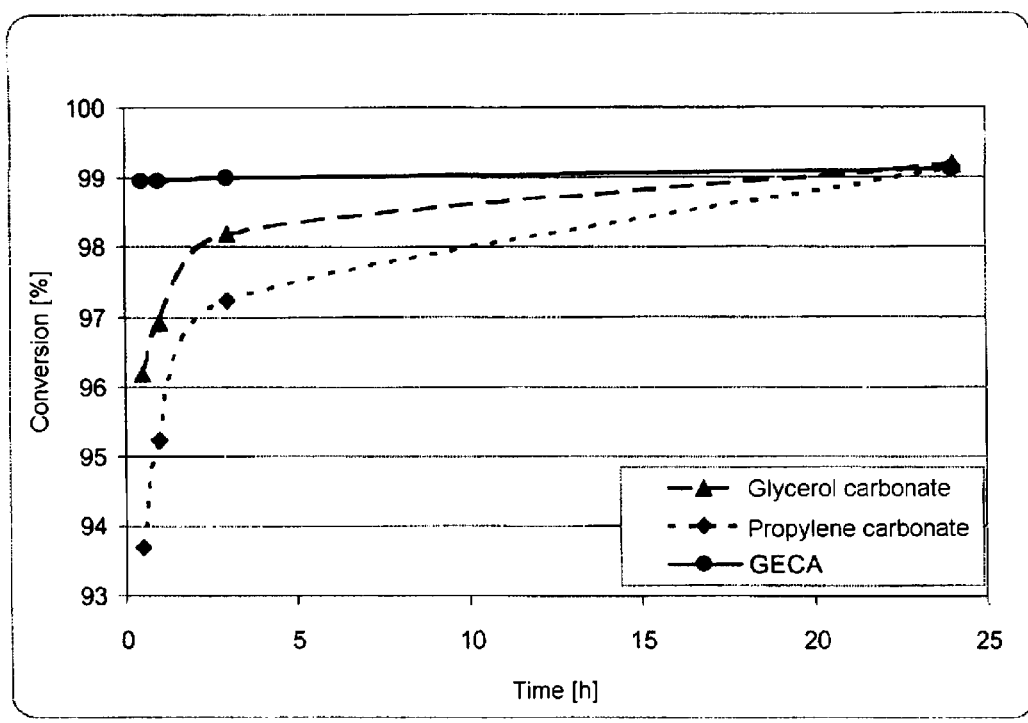

2-OXO-1, 3-DIOXOLANE-4-CARBOXYLIC ACID AND DERIVATIVES THEREOF, THEIR PREPARATION AND USE

This application claims the benefit of the filing date of U.S. Provisional Application Ser. No. 61/355,566, filed Jun. 17, 2010, incorporated herein by reference.

The present disclosure relates to 2-Oxo-1,3-dioxolane-4-carboxylic acid and derivatives thereof, according to the general formula (V)

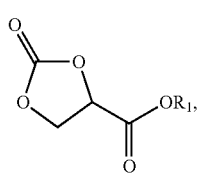

(V)

in which $R_1$ represents a negative charge, hydrogen or may be Me or Et or an n-valent radical, which may be substituted with at most n−1 further 2-oxo-1,3-dioxolane-4-carboxyl groups, as well as a process for their preparation by means of carboxylation of the corresponding epoxides, a process for their transesterification and their use for the preparation of hydroxyurethanes and as end groups for the blocking of amines.

WO2004/003001 A1 describes compounds of the general formula (I)

(I)

where $R_1$ and $R_2$ may be radicals independent of one another, $R_1+R_2=O$ or $CR_1+R_2$ may be a 3-6-membered cycloalkyl group. $R_4$ may be hydrogen, straight-chain or branched $C_{1-8}$-alkyl, $C_{5-12}$-cycloalkyl or $C_{6-15}$-aryl. $R_3$ may be straight-chain or branched $C_{1-5}$-alkyl or $C_{6-15}$-aryl. In general, WO2004/003001 describes the enzymatic racemate separation of the enantiomers of type (I) but without indicating a synthesis for these compounds.

EP 1941946 A1 describes the use of a carbonitride catalyst inter alia for the preparation of certain disubstituted organic carbonates. These may also be compounds of the general formula (II),

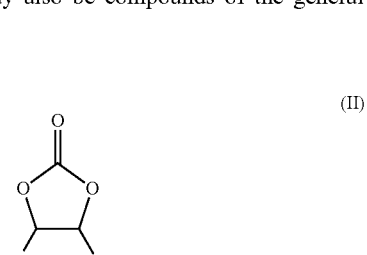

(II)

where $R^{10}$ and $R^{11}$, independently of one another, are selected optional substituents. Possible meanings of the substituents are alkyl, aryl, heteroaryl and ester groups $CO_2A$, where A may in turn be alkyl or aryl, e.g. straight-chain or branched $C_{1-6}$-alkyl, preferably $C_{1-3}$-alkyl and particularly preferably methyl or ethyl. However, no syntheses for 2-oxo-1,3-dioxolane systems are stated.

JP 2006-003433 A discloses a sealing composition for liquid crystal display elements which comprises a compound of the general formula (III),

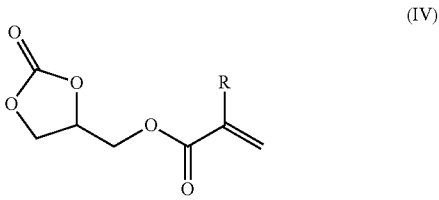

(III)

where R is H, a hydroxyl group, a cyano group, a carboxylic acid group, an optionally substituted aromatic ring, a straight-chain, branched or cyclic alkyl group, an acyl group or an ester group. However, it is not stated in what direction the ester group points and which further radical it carries. Neither is any specific synthesis for these 2-oxo-1,3-dioxolane systems stated.

EP 0001088 A1 describes inter alia 2-oxo-1,3-dioxolanes of the general formula (IV), where R can be H or $CH_3$.

(IV)

Polyurethanes based on polyisocyanates belong to the prior art. These are used for example as adhesives, sealants, casting compositions, as corrosion protection and for coatings. The high resistance to acid, alkalis and chemicals of the cured compositions obtained in this way are advantageous. However, monomeric low molecular weight (poly)isocyanate compounds are toxicologically unacceptable, especially if they are readily volatile or migrate.

Polyurethane systems can also be obtained starting from cyclic carbonate compounds which are toxicologically acceptable. Thus, glycerol carbonate (4-(hydroxymethyl)-2-oxo-1,3-dioxolane) is used in cosmetics, for example. Cyclic carbonate compounds react with amines to give hydroxyurethanes.

However, simple cyclic carbonates such as e.g. 4-methyl-2-oxo-1,3-dioxolane or said 4-(hydroxymethyl)-2-oxo-1,3-dioxolane are not particularly reactive. Studies have been carried out, cf. H. Tomita, F. Sanda, T. Endo, Journal of Polymer Science: Part A: Polymer Chemistry, Vol. 39, 3678-3685 (2001), according to which the reactivity of the 2-oxo-1,3-dioxolanes substituted in 4-position by the group R with amines increases in the order: R=Me<R=H<R=Ph<R=$CH_2$OPh<<R=$CF_3$. Unfortunately, such fluorinated compounds are not readily accessible, expensive and (e.g. in the event of fire) potentially toxic. Moreover, low molecular weight monomeric 2-oxo-1,3-dioxolanes are not suitable as binders. Rather, reactive functional groups for example in 4-position are required in order to prepare relatively high molecular weight multifunctional binders which can then be reacted with amines for the polyurethane formation. The industrial accessibility of these 2-oxo-1,3-dioxolanes also plays an important role.

It is desirable to essentially avoid at least some of the disadvantages of the prior art described above. In particular, a 2-oxo-1,3-dioxolane system is provided which is acceptable, readily accessible and highly reactive with amines and carries at least one further reactive functional group.

Provided is 2-Oxo-1,3-dioxolane-4-carboxylic acid, or a derivative thereof, according to the general formula (V),

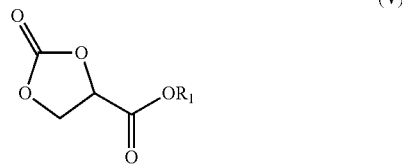

(V)

wherein $R_1$ represents a negative charge, hydrogen, or a group selected from straight-chain or branched aliphatic groups, aryl groups, aralkyl groups and alkylaryl groups.

In case $R_1$ represents a negative charge, the counterion to compensate that charge may be selected from alkali metal and alkaline earth metal cations, in certain embodiments selected from $Li^+$, $Na^+$, $K^+$, and $\frac{1}{2}Ca^{2+}$. The subject derivative is thus an alkali metal or alkaline earth metal salt. In case $R_1$ represents hydrogen, the subject compound is thus 2-Oxo-1,3-dioxolane-4-carboxylic acid.

In case $R_1$ represents a group selected from straight-chain or branched aliphatic groups, aryl groups, aralkyl groups and alkylaryl groups the said derivative is thus an ester. In particular $R_1$ represents a $C_{1-12}$-alkyl group.

$R_1$ may, for example, be selected from methyl, ethyl, n-propyl, isopropyl, n-butyl, sec-butyl, tert-butyl, n-pentyl, neopentyl, n-hexyl, 2-ethyl-n-hexyl, n-lauryl, cyclohexyl, phenyl and benzyl.

In particular, the 2-oxo-1,3-dioxolane-4-carboxylic acid ester may be 4-methoxycarbonyl-2-oxo-1,3-dioxolane or 4-ethoxycarbonyl-2-oxo-1,3-dioxolane.

However, it is likewise possible that $R_1$ is an n-valent radical derived by abstraction of the OH groups of an n-valent polyol which may be substituted by at most n−1 further 2-oxo-1,3-dioxolane-4-carboxylate groups of the general formula (VI)

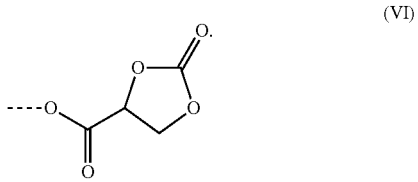

(VI)

If fewer than n−1 further 2-oxo-1,3-dioxolane-4-carboxylate groups are present, $R_1$ is additionally substituted with the stoichiometrically required number of OH groups.

In these relatively high molecular weight 2-oxo-1,3-dioxolane-4-carboxylic acid esters, the n-valent polyol can comprise for example $C_{2-4}$-(poly)oxyalkylene groups, i.e. groups derived from ethylene oxide, propylene oxide and/or butylene oxide and having one or more oxyalkylene repeat units. In certain embodiments, n=2 to 5. Examples of such relatively high molecular weight multifunctional compounds suitable as binders are discussed below.

A further subject matter of the present application is considered to be the preparation of the low molecular weight monomeric 2-oxo-1,3-dioxolane-4-carboxylic acid esters. These 2-oxo-1,3-dioxolane-4-carboxylic acid esters can be prepared for example by reacting the corresponding epoxides of the formula (VII), where $R_1$ has the stated meaning, with $CO_2$.

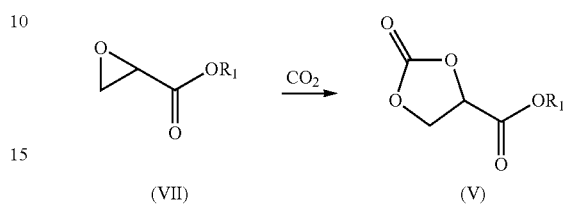

(VII)  (V)

Epoxides of the formula (VII) are commercially available compounds well-known in the prior art which can be prepared for example by means of epoxidation of the corresponding acrylic acid esters (VIII); for $R_1$=Me, cf. e.g. Organic Syntheses, Vol. 83, p. 162 (2006):

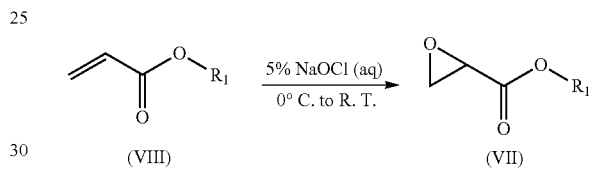

(VIII)  (VII)

Alternative syntheses are also known; for $R_1$=Et cf. e.g. Organic Syntheses, Coll. Vol. 10, p. 401 (2004); Vol. 75, p. 37 (1998).

The temperature of the aforementioned reaction with $CO_2$ can be varied within wide ranges. It may expediently be in the range from 15° C. to 150° C., optionally in the range from 30° C. to 100° C., and in particular embodiments in the range from 60° C. to 80° C. The reaction can be carried out in open apparatuses at ambient pressure (ca. 1 bar), for example by means of passing gaseous $CO_2$ through a suitable reaction solution. However, the reaction can also take place in closed systems at an increased pressure, for example at a pressure of from 1 bar to 100 bars, optionally from 20 bars to 100 bars, and in particular embodiments at about 80 bars.

The reaction with $CO_2$ can take place without a solvent since the starting materials and the products are generally liquid. However, it has proven to be expedient to carry out the reaction in polar aprotic solvents. A nonexhaustive list of suitable solvents includes tetrabutyl methyl ether, acetonitrile, acetone, tetrahydrofuran, dimethyl carbonate, toluene, xylene, N-methyl-2-pyrrolidone, N-ethyl-2-pyrrolidone, and mixtures thereof.

The reaction with $CO_2$ can generally be carried out without catalyst. However, the procedure expediently involves working in the presence of a catalyst which is selected from metal halides and halogen salts of organic nitrogen compounds, and mixtures thereof.

As has been established above, low molecular weight, monomeric 2-oxo-1,3-dioxolane-4-carboxylic acid esters are not suitable as binders. However, the $COOR_1$ group has the advantage that it is available for further reactions. Thus, relatively high molecular weight, multifunctional representatives of the compound of the general formula (V) can be prepared by means of transesterification. Accordingly, a process for the preparation of these relatively high molecular weight multifunctional esters is considered to be a further subject matter of the present application, where a low molecular weight, monomeric 2-oxo-1,3-dioxolane-4-carboxylic acid ester of the general formula (V) is transesterified with an n-valent polyol.

In said process, the transesterification is carried out in the presence of an enzymatic catalyst or an acidic cation exchanger. One of the difficulties which was associated with this transesterification reaction was to find catalysts which catalyse the transesterification at the —COOR$_1$ group, but do not lead to attacks on the —O—COO— group. The aforementioned catalysts circumvent these difficulties. Novozym® 435 from Novozymes A/S, an immobilized lipase, and the H$^+$ form of Amberlite® 200 from Rohm & Haas Company, i.e. a strongly acidic cation exchanger, have proven to be suitable.

The polyol and the low molecular weight 2-oxo-1,3-dioxolane-4-carboxylic acid ester may be used in stoichiometric fractions, where the conversion of the transesterification may be above 80%, based on the low molecular weight 2-oxo-1,3-dioxolane-4-carboxylic acid ester used. The reaction temperature is in the range from 50 to 100° C., in which case Novozym® 435 may be used at about 50 to 80° C. and Amberlite® 200 may be used at about 100° C. The transesterification with Novozym® 435 can expediently be carried out without solvents; the transesterification with Amberlite® 200 is expediently carried out in a suitable solvent. The reaction may be expediently carried out until essentially the calculated amount of R$_1$—OH has been distilled off.

Suitable polyols are, for example, diols, in particular embodiments glycols, triols and tetraols, such as e.g. 1,4-butanediol, neopentyl glycol (2,2-dimethylolpropane), 1,1,1-trimethylolpropane, pentaerythritol and tetramethylolmethane. Said polyols can also be modified with C$_{2-4}$-alkylene oxides, in particular ethylene oxide and propylene oxide. In general, it is possible to use all polyols which can also be used for the preparation of conventional polyurethanes.

Alternatively, it is possible to firstly transesterify low molecular weight acrylic acid esters with said polyols, then to epoxidize them and then to carboxylate them with CO$_2$. This gives compounds which likewise fall under the general formula (V).

Further provided is the use of the 2-oxo-1,3-dioxolane-4-carboxylic acid esters for the preparation of hydroxyurethanes. The subject cyclic carbonate compounds react with amines to give hydroxyurethanes.

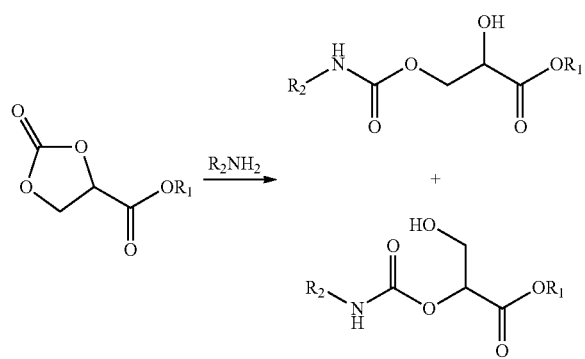

Here in principle two different hydroxyurethanes are possible, namely hydroxyurethanes with primary or secondary hydroxyl groups. In this respect, it has been shown that the electron-withdrawing COOR$_1$ group diverts the reaction essentially in the direction of the hydroxyurethanes with secondary hydroxyl groups since, in the event of attack of the nucleophilic nitrogen atom, the negative charge on the oxygen atom which is closer to the COOR$_1$ group is better stabilized. Hydroxyurethanes with secondary hydroxyl groups have the additional advantage that the back-reaction is hindered. Theoretically, an attack of the amine at the ester group would also be conceivable; however, it was shown analytically that the amine essentially attacks only the 2-oxo-1,3-dioxolane group.

Suitable amines are primary and secondary amines with alkyl groups, aryl groups, aralkyl groups, and alkylaryl groups as radicals. Primary amines react more quickly than secondary amines; aliphatic amines react more quickly than aromatic amines. As regards the relative reactivities of different amines, compare C. Diakoumakos, D. Kotzev, Non-Isocyanate-Based Polyurethanes Derived upon the Reaction of Amines with Cyclocarbonate Resins, Macromol. Symp., 216, 37-46 (2004), in particular scheme 4 on p. 45. All of the amines specified therein are also suitable for carrying out the present process. Relatively high molecular weight amines such as e.g. Jeffamine® from Huntsman Corp. and polyether amines from BASF SE are also suitable.

As is shown below by reference to examples, the subject 2-oxo-1,3-dioxolane-4-carboxylic acid esters are significantly more reactive towards amines than for example the comparable compounds glycerol carbonate (4-(hydroxymethyl)-2-oxo-1,3-dioxolane) and propylene carbonate (4-methyl-2-oxo-1,3-dioxolane). This is true both for the low molecular weight representatives and also for the relatively high molecular weight representatives. The reactivity of the subject 4-methoxycarbonyl-2-oxo-1,3-dioxolane towards amines may be in the order of magnitude of the 4-trifluoromethyl-2-oxo-1,3-dioxolane investigated in "H. Tomita, F. Sanda, T. Endo, Journal of Polymer Science: Part A: Polymer Chemistry, Vol. 39, 3678-3685 (2001)", but without having the disadvantages of the CF$_3$ group described above.

An additional advantage of the polyhydroxyurethane systems lies in the higher hydrophilicity of these systems, which can be attributed to the OH groups present. These OH groups are in principle also available for the crosslinking with polyisocyanates, although the isocyanate-free systems possible according to the subject process are preferred on account of their lower toxicity.

Moreover, when producing polyhydroxyurethane systems which are based on 2-oxo-1,3-dioxolanes, bubble formation as a result of CO$_2$ that is formed may not arise, even in the presence of moisture. Consequently, largely pore- and bubble-free coatings are possible, which is sometimes problematic for classic polyurethane systems. Furthermore, the thermal stability of such polyhydroxyurethane systems is also higher than the stability of classic polyurethane systems.

Moreover, the low molecular weight 2-oxo-1,3-dioxolane-4-carboxylic acid esters can be used to block amines as end groups (so-called "end caps"), which constitutes a further subject matter of the present application. This is also of interest with regard to conventional, amine-crosslinked polyurethane systems since an amine excess can lead to discolorations, while an isocyanate excess is toxicologically unacceptable.

Figure 2:
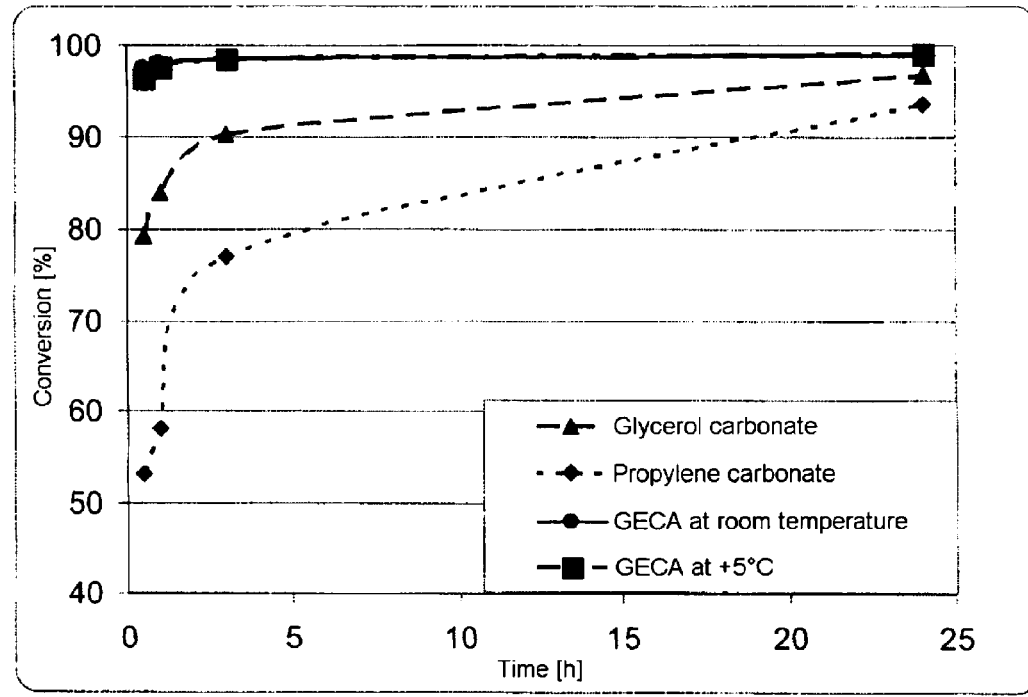
Figure 3:
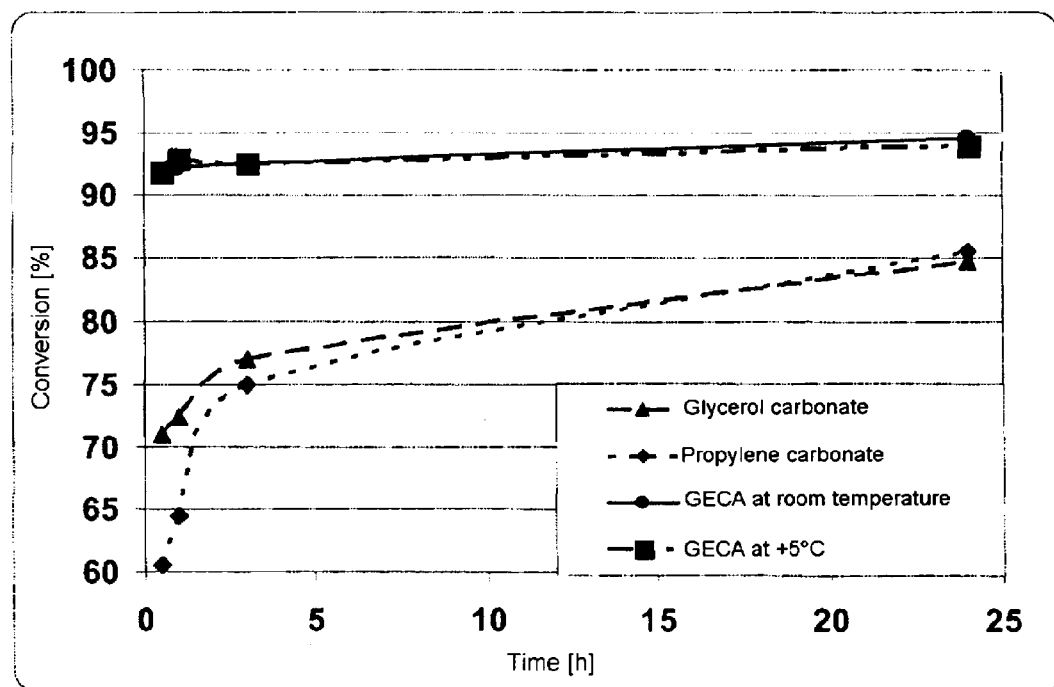
Figure 4:
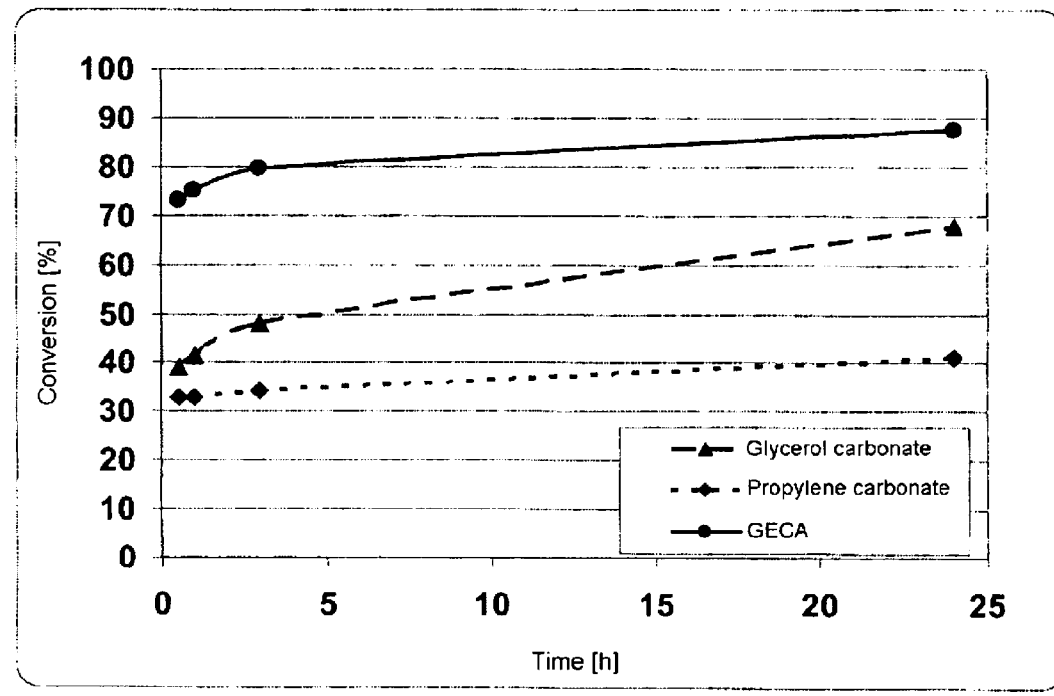
Figure 5:
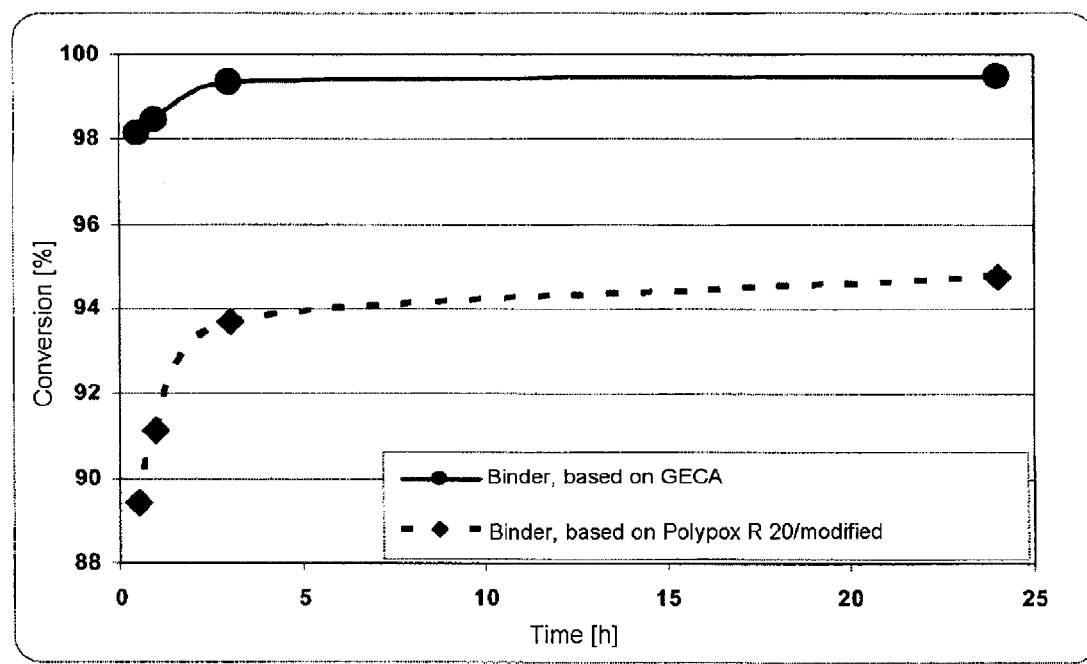

The present embodiments are now illustrated in more detail using the examples below with reference to the attached drawings. These show:

FIG. 1 the progress over time of the reaction of various 2-oxo-1,3-dioxolanes with ethanolamine, FIG. 2 the progress over time of the reaction of various 2-oxo-1,3-dioxolanes with benzylamine, FIG. 3 the progress over time of the reaction of various 2-oxo-1,3-dioxolanes with isophoronediamine, FIG. 4 the progress over time of the reaction of various 2-oxo-1,3-dioxolanes with Jeffamin® D 400, FIG. 5 the progress over time of the reaction of various binders based on 2-oxo-1,3-dioxolanes with n-butylamine.

EXAMPLE 1a

Preparation of 4-methoxycarbonyl-2-oxo-1,3-dioxolane

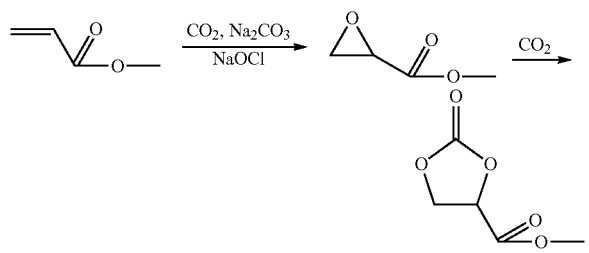

80 g of sodium carbonate were dissolved in 200 ml of distilled water in a 1000 ml three-neck flask. The solution was cooled to 10° C. 58.5 g of methyl acrylate were then added and, after ca. 10 minutes, likewise at 10° C., 400 ml of a 7% strength aqueous sodium hypochlorite solution were stirred in. Then, the system was immediately flushed intensively with $CO_2$. The temperature was allowed to increase to room temperature. The flask was flushed intensively with $CO_2$ for a further 1 hour at ca. 25 to 30° C., during which the temperature was held in the stated range through occasional cooling with an ice bath. The resulting white solid was filtered off via a suction filter. The filtrate was extracted with 4×90 ml of dichloromethane. The combined organic phase was dried with sodium sulphate and filtered off. The filtrate was removed on a rotary evaporator. Methyl epoxypropionate was obtained in 50 to 60% yield and a purity of 97%.

20 g of the methyl epoxypropionate were mixed with 20 g of tert-butyl methyl ether and 1 g of tetrabutylammonium bromide. The homogeneous mixture was transferred to a 100 ml pressurized reactor and carboxylated for 4 days at 40° C. and a $CO_2$ pressure of 20 bar. Following carboxylation, a two-phase system was obtained; the upper phase consisted of tert-butyl methyl ether, and the lower phase consisted of 4-methoxycarbonyl-2-oxo-1,3-dioxolane (purity 94% (GC), yield 94%).

The product was characterized as follows: $^1$H NMR (500 MHz, $CDCl_3$) δ: 3.82 (3H, s, $CH_3$), 4.50 (1H, dd, J=5.5, 9.0, $CH_2$), 4.66 (1H, dd, J=9.0, 9.0, $CH_2$), 5.09 (1H, dd, J=9.0, 5.5, CH); $^{13}$C NMR (125 MHz, $CDCl_3$) δ: 53.81 ($CH_3$), 67.00 ($CH_2$), 72.34 (CH), 153.97 (—O—CO—O—), 167.42 (—CO—O—); IR (neat): 1812 $cm^{-1}$, (—O—CO—O—), 1742 $cm^{-1}$ (—CO—O—).

EXAMPLE 1b

Preparation of 4-ethoxycarbonyl-2-oxo-1,3-dioxolane

Example 1a was repeated as described hereinabove, with the exception that ethyl acrylate was used instead of methyl acrylate. The results were essentially as stated in example 1a, with the exception that 4-ethoxycarbonyl-2-oxo-1,3-dioxolane was obtained.

EXAMPLE 2

Preparation of 4-methoxycarbonyl-2-oxo-1,3-dioxolane

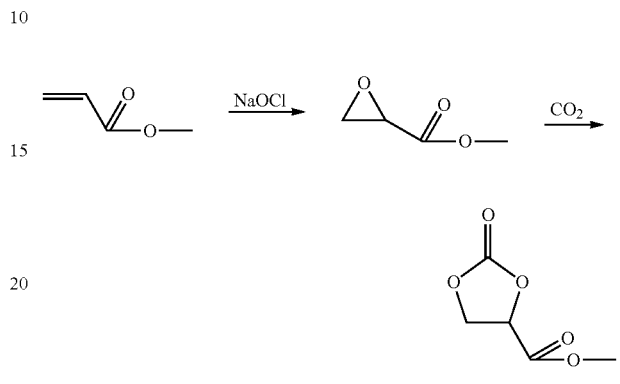

940 ml of a 7% strength aqueous sodium hypochlorite solution were introduced as initial charge in a 2000 ml three-neck flask. The solution was cooled to 0° C. with the help of an ice/salt water bath. 58.5 g of methyl acrylate were then added and the mixture was held at 0° C. for 30 minutes. The low-temperature mixture was then removed and further stirred for ca. 1.5 hours such that the mixture heated up by itself (65-70° C.). A colourless, cloudy solution was formed. Then, the solution was cooled to room temperature and extracted with 4×150 ml of dichloromethane. The combined organic phase was dried with magnesium sulphate and filtered off. The filtrate was removed on a rotary evaporator. Methyl epoxypropionate was obtained in 70 to 80% yield and a purity of 97%. The further reaction to the 4-methoxycarbonyl-2-oxo-1,3-dioxolane proceeded as described in Example 1.

EXAMPLE 3

Preparation of 4-methoxycarbonyl-2-oxo-1,3-dioxolane

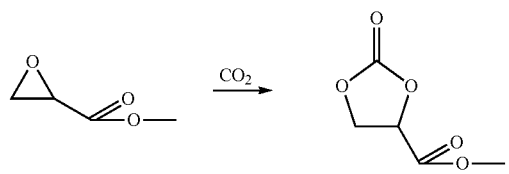

20 g of methyl epoxypropionate were mixed with 20 g of acetonitrile, 1.5 g of benzyl-trimethylammonium chloride and 1.5 g of $ZnBr_2$. The homogeneous mixture was transferred to a 100 ml pressurized reactor and carboxylated for 6 days at 25° C. and a $CO_2$ pressure of 30 bar. Following carboxylation, the mixture was diluted with 100 g of acetonitrile. The mixture was purified with aluminium oxide and activated carbon. Then, the acetonitrile was distilled off. This gave 4-methoxycarbonyl-2-oxo-1,3-dioxolane (purity 72% (GC), yield 65%).

EXAMPLE 4

Preparation of 4-methoxycarbonyl-2-oxo-1,3-dioxolane

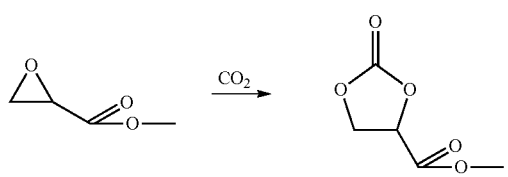

20 g of methyl epoxypropionate were mixed with 20 g of tert-butyl methyl ether, 1.5 g of tetrabutylammonium bromide and 1.5 g of potassium iodide. The homogeneous mixture was transferred to a 100 ml pressurized reactor and carboxylated for 6 days at 50° C. and a $CO_2$ pressure of 30 bar. Following the carboxylation, a two-phase system was obtained; the upper phase consisted of tert-butyl methyl ether, and the lower phase consisted of 4-methoxycarbonyl-2-oxo-1,3-dioxolane (purity 83% (GC), yield 79%).

EXAMPLE 5

Preparation of Binder 1

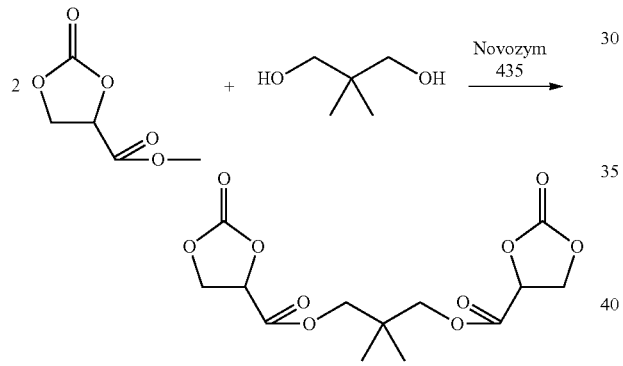

0.2 mol of 4-methoxycarbonyl-2-oxo-1,3-dioxolane ("GECA") were mixed with 0.1 mol of neopentyl glycol (Sigma-Aldrich). 5% by weight (based on GECA) of Novozym® 435 (Novozymes A/S) were added thereto. The mixture was stirred and heated to 55 to 60° C. After 72 hours, 0.2 mol of methanol had distilled off and the reaction was complete.

EXAMPLE 6

Preparation of Binder 2

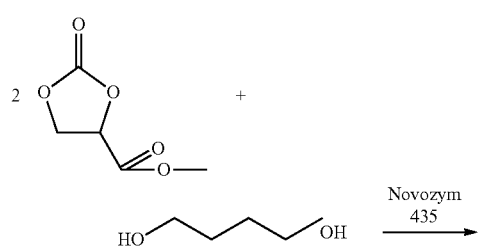

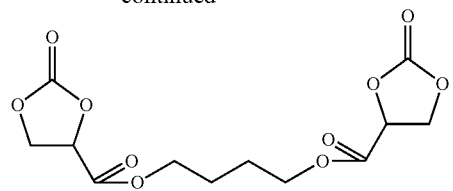

0.2 mol of 4-methoxycarbonyl-2-oxo-1,3-dioxolane ("GECA") were mixed with 0.1 mol of 1,4-butanediol (Sigma-Aldrich). 5% by weight (based on GECA) of Novozym® 435 (Novozymes A/S) were added thereto. The mixture was stirred and heated to 55 to 60° C. After 72 hours, 0.2 mol of methanol had distilled off and the reaction was complete.

EXAMPLE 7

Preparation of Binder 3

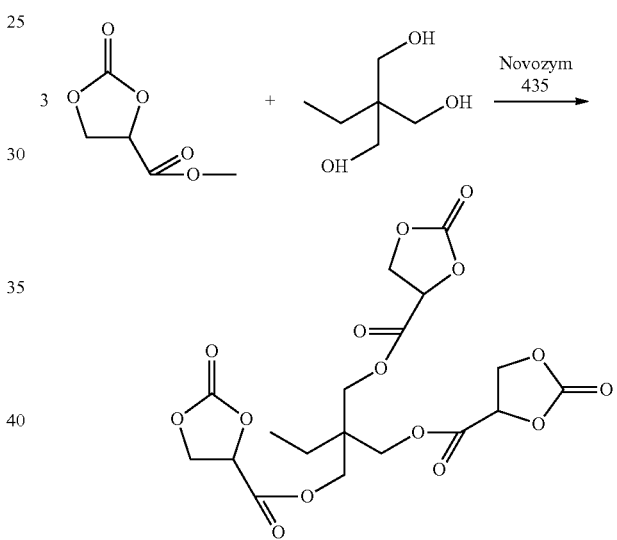

0.3 mol of 4-methoxycarbonyl-2-oxo-1,3-dioxolane ("GECA") were mixed with 0.1 mol of 1,1,1-trimethylolpropane (Sigma-Aldrich). 5% by weight (based on GECA) of Novozym® 435 (Novozymes A/S) were added thereto. The mixture was stirred and heated to 55 to 60° C. After 72 hours, 0.3 mol of methanol had distilled off and the reaction was complete.

EXAMPLE 8

Preparation of Binder 4

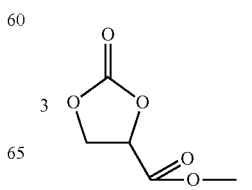

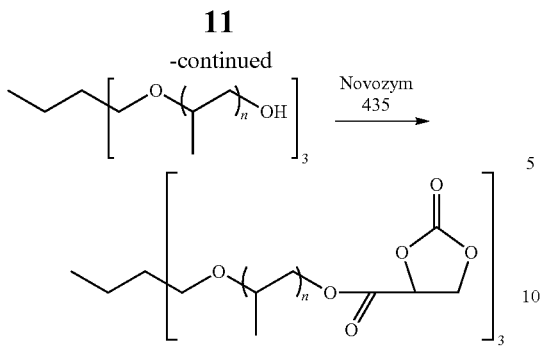

0.3 mol of 4-methoxycarbonyl-2-oxo-1,3-dioxolane ("GECA") were mixed with 0.1 mol of 1,1,1-trimethylolpropane propoxylate (Sigma-Aldrich, average molecular weight (MO ca. 308). 5% by weight (based on GECA) of Novozym® 435 (Novozymes A/S) were added thereto. The mixture was stirred and heated to 55 to 60° C. After 72 hours, 0.3 mol of methanol had distilled off and the reaction was complete.

EXAMPLE 9

Preparation of Binder 1

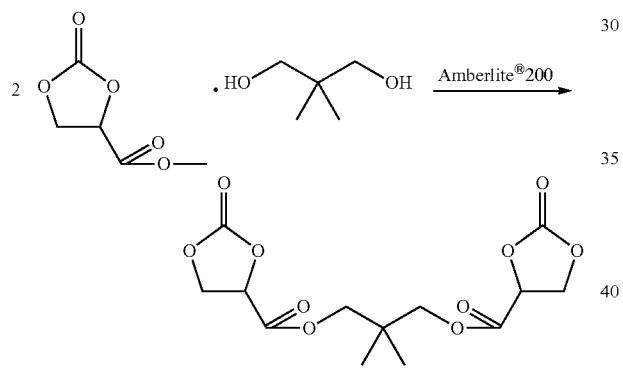

0.2 mol of 4-methoxycarbonyl-2-oxo-1,3-dioxolane ("GECA") were mixed with 0.1 mol of neopentyl glycol (Sigma-Aldrich) and 200 ml of cyclohexane. 5% by weight (based on GECA) of Amberlite® 200 (Fluka) were added thereto. The mixture was stirred at 100° C. on a water separator. After 5 hours, 0.2 mol of methanol had separated off and the reaction was complete.

EXAMPLE 10

Preparation of Binder 3

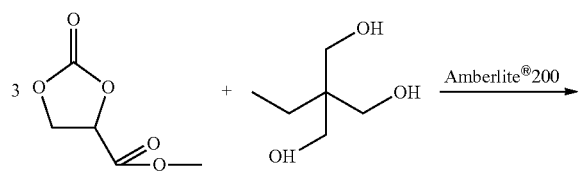

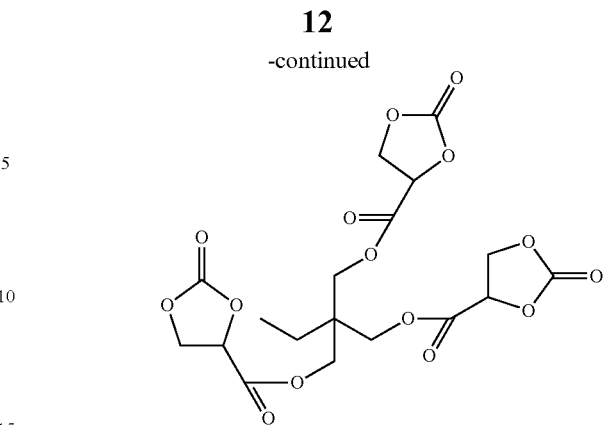

0.3 mol of 4-methoxycarbonyl-2-oxo-1,3-dioxolane ("GECA") were mixed with 0.1 mol of 1,1,1-trimethylolpropane (Sigma-Aldrich). 5% by weight (based on GECA) of Amberlite® 200 (Fluka) were added thereto. The mixture was stirred at 100° C. on a water separator. After 5 hours, 0.3 mol of methanol had separated off and the reaction was complete.

EXAMPLE 11

Reaction of 2-oxo-1,3-dioxolanes with ethanolamine 0.1 mol of ethanolamine were mixed with 0.1 mol of 4-methoxycarbonyl-2-oxo-1,3-dioxolane ("GECA") and stirred at room temperature. After 0.5 h, 1 h, 3 h and 24 h, the amine number was determined by means of titration and used to calculate the conversion. This procedure was also carried out with 4-methyl-2-oxo-1,3-dioxolane ("propylene carbonate") and 4-(hydroxymethyl)-2-oxo-1,3-dioxolane ("glycerol carbonate"). The results are reproduced graphically in FIG. 1 and show the high reactivity of 4-methoxycarbonyl-2-oxo-1,3-dioxolane.

EXAMPLE 12

Reaction of 2-oxo-1,3-dioxolanes with benzylamine

Example 11 was repeated using benzylamine instead of ethanolamine. 4-Methoxycarbonyl-2-oxo-1,3-dioxolane ("GECA") was investigated both at room temperature and also at +5° C., whereas 4-methyl-2-oxo-1,3-dioxolane ("propylene carbonate") and 4-(hydroxymethyl)-2-oxo-1,3-dioxolane ("glycerol carbonate") were tested just at room temperature. The results are reproduced graphically in FIG. 2 and impressively show the exceptional reactivity of 4-methoxycarbonyl-2-oxo-1,3-dioxolane (even at +5° C.).

EXAMPLE 13

Reaction of 2-oxo-1,3-dioxolanes with isophoronediamine 0.1 mol of isophoronediamine was mixed with 0.2 mol of 4-methoxycarbonyl-2-oxo-1,3-dioxolane ("GECA") and stirred at room temperature. After 0.5 hours, 1 hour, 3 hours and 24 hours, the amine number was determined by means of titration and used to calculate the conversion. This procedure was also carried out with 4-methoxycarbonyl-2-oxo-1,3-dioxolane ("GECA") at +5° C. and with 4-methyl-2-oxo-1,3-dioxolane ("propylene carbonate") and 4-(hydroxymethyl)-2-oxo-1,3-dioxolane ("glycerol carbonate") at room temperature. The results are reproduced graphically in FIG. 3 and impressively show the exceptional reactivity of 4-methoxycarbonyl-2-oxo-1,3-dioxolane (even at +5° C.).

EXAMPLE 14

Reaction of 2-oxo-1,3-dioxolanes with Jeffamin® D 400

Example 13 was repeated using Jeffamin® D 400. Since the reaction with high molecular weight amines generally proceeded more slowly than with low molecular weight amines, the 4-methoxycarbonyl-2-oxo-1,3-dioxolane (GECA) was also only investigated at room temperature. The results are reproduced graphically in FIG. 4 and also show in the present case the high reactivity of 4-methoxycarbonyl-2-oxo-1,3-dioxolane.

EXAMPLE 15

Reaction of Binder 3 Compared to the Prior Art 0.1 mol of binder 3 from example 7 or 10 was mixed with 0.3 mol of n-butylamine and stirred at room temperature. After 0.5 hours, 1 hour, 3 hours and 24 hours, the amine number was determined by means of titration and used to calculate the conversion. This procedure was also carried out with carboxylated Polypox® R20 (UPPC AG), a trifunctional epoxide which was carboxylated with $CO_2$ by ourselves,

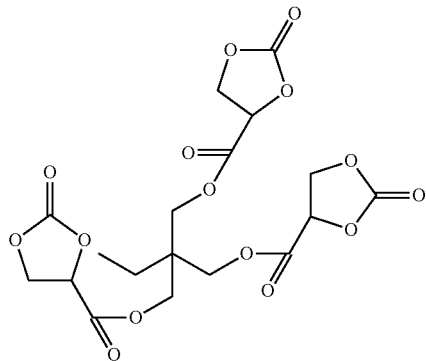 [SMILES: CCC(COC(=O)C1COC(=O)O1)(COC(=O)C1COC(=O)O1)COC(=O)C1COC(=O)O1]

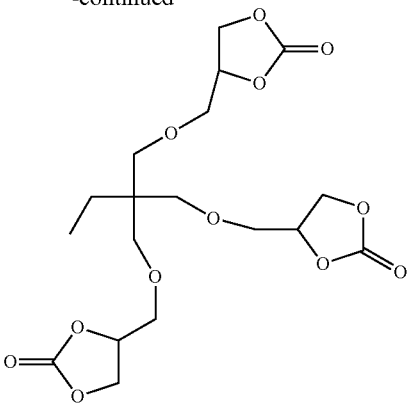

at room temperature. The results are reproduced graphically in FIG. 5 and show the exceptional reactivity of our binder.

EXAMPLE 16

Film Formation with Isophoronediamine 0.000666 mol of binder 3 from example 7 or 10 was mixed with 0.001 mol of isophoronediamine (binder in excess). The two components were stirred together by hand for 20 seconds, after which a film 300 μm in thickness was drawn (pot time 2 min, tack-free after 6 hours).

EXAMPLE 17

Film Formation with 1,3-cyclohexanebis(methylamine)

0.000666 mol of binder 3 from example 7 or 10 was mixed with 0.001 mol of 1,3-cyclo-hexanebis(methylamine) (binder in excess). The two components were stirred together by hand for 20 seconds, after which a film 300 μm in thickness was drawn (pot time 2 min, tack-free after 7 hours).

Although the embodiments have been described in detail through the above description and the preceding examples, these examples are for the purpose of illustration only and it is understood that variations and modifications can be made by one skilled in the art without departing from the spirit and the scope of the disclosure. It should be understood that the embodiments described above are not only in the alternative, but can be combined.

We claim:
1. A 2-Oxo-1,3-dioxolane-4-carboxylic acid ester according to formula (V), wherein $R_1$ is selected from methyl, ethyl, n-propyl, isopropyl, n-butyl, sec-butyl, tert-butyl, n-pentyl, neopentyl, n-hexyl, 2-ethyl-n-hexyl, n-lauryl, cyclohexyl, and phenyl.

2. The 2-Oxo-1,3-dioxolane-4-carboxylic acid ester according to claim 1, selected from 4-methoxycarbonyl-2-oxo-1,3-dioxolane and 4-ethoxycarbonyl-2-oxo-1,3-dioxolane.

3. A 2-Oxo-1,3-dioxolane-4-carboxylic acid ester according to formula (V),

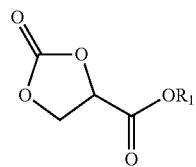

(V)

wherein $R_1$ is a radical having a valency of 2 to 5 derived by abstraction of all OH groups of a polyol having a valency of 2 to 5 and which is substituted by an amount of further 2-oxo-1,3-dioxolane-4-carboxylate groups of formula (VI)

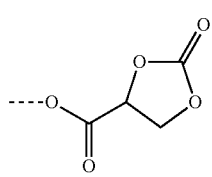

(VI)

equal to the radical valency minus 1.

4. The 2-Oxo-1,3-dioxolane-4-carboxylic acid ester according to claim 3, wherein the polyol comprises $C_{2-4}$-(poly)oxyalkylene groups.

5. A process for the preparation of a 2-oxo-1,3-dioxolane-4-carboxylic acid ester according to claim 1, wherein an epoxide of formula (VII), is reacted with $CO_2$,

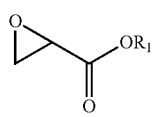

(VII)

wherein $R_1$ is selected from methyl, ethyl, n-propyl, isopropyl, n-butyl, sec-butyl, tert-butyl, n-pentyl, neopentyl, n-hexyl, 2-ethyl-n-hexyl, n-lauryl, cyclohexyl, and phenyl.

6. The process according to claim 5, wherein the reaction is carried out at a temperature of from 15° C. to 150° C., optionally from 30° C. to 100° C., and at a pressure of from 1 bar to 100 bars, optionally from 20 bars to 100 bars.

7. The process according to claim 5, wherein the reaction is carried out without solvent or in a polar aprotic solvent.

8. The process according to claim 5, wherein the reaction is carried out in the presence of a catalyst selected from metal halides and halogen salts of organic nitrogen compounds and mixtures thereof.

9. The process according to claim 5, wherein the 2-oxo-1,3-dioxolane-4-carboxylic acid ester is selected from 4-methoxycarbonyl-2-oxo-1,3-dioxolane and 4-ethoxycarbonyl-2-oxo-1,3-dioxolane.

10. The process for the preparation of a 2-oxo-1,3-dioxolane-4-carboxylic acid ester according to claim 3, wherein the 2-oxo-1,3-dioxolane-4-carboxylic acid ester,
   in which $R_1$ is selected from methyl, ethyl, n-propyl, isopropyl, n-butyl, sec-butyl, tert-butyl, n-pentyl, neopentyl, n-hexyl, 2-ethyl-n-hexyl, n-lauryl, cyclohexyl, and phenyl,
is transesterified with a polyol having a valency of 2 to 5, optionally wherein the polyol comprises $C_{2-4}$-(poly)oxyalkylene groups.

11. The process according to claim 10, wherein the transesterification is carried out in the presence of an enzymatic catalyst or an acidic cation exchanger.

12. The process according to claim 10, wherein the 2-oxo-1,3-dioxolane-4-carboxylic acid ester is selected from 4-methoxycarbonyl-2-oxo-1,3-dioxolane and 4-ethoxycarbonyl-2-oxo-1,3-dioxolane.

13. The 2-Oxo-1,3-dioxolane-4-carboxylic acid ester according to claim 3, wherein the polyol is selected from the group consisting of diol, glycol, triol, tetraol, 1,4-butanediol, neopentyl glycol (2,2-dimethylolpropane), 1,1,1-trimethylolpropane, pentaerythritol and tetramethylolmethane, optionally modified with $C_{2-4}$-alkylene oxide.

* * * * *